United States Patent
Einav et al.

(10) Patent No.: US 8,701,498 B2
(45) Date of Patent: Apr. 22, 2014

(54) DEVICE FOR DETERMINING MATERIAL PROPERTIES

(75) Inventors: Itai Einav, Willoughby (AU); Pierre Rognon, Annadale (AU); Thomas Miller, Maroubra (AU)

(73) Assignee: The University of Sydney, Sydney, NSW (AU)

( * ) Notice: Subject to any disclaimer, the term of this patent is extended or adjusted under 35 U.S.C. 154(b) by 90 days.

(21) Appl. No.: 13/538,628

(22) Filed: Jun. 29, 2012

(65) Prior Publication Data

US 2013/0269444 A1 Oct. 17, 2013

(30) Foreign Application Priority Data

Apr. 12, 2012 (AU) ................................ 2012901433

(51) Int. Cl.
*G01B 5/30* (2006.01)
*G01B 7/16* (2006.01)
*G01L 1/00* (2006.01)
*G01N 3/00* (2006.01)

(52) U.S. Cl.
USPC .......... 73/760; 73/862.08; 73/488; 73/884.81

(58) Field of Classification Search
USPC ......................... 73/760, 864.81, 862.08, 488
See application file for complete search history.

(56) References Cited

U.S. PATENT DOCUMENTS

| | | | |
|---|---|---|---|
| 4,578,988 A * | 4/1986 | Hori et al. ..................... | 73/54.01 |
| 2001/0054318 A1 * | 12/2001 | Mallick et al. .................. | 73/818 |
| 2003/0218258 A1 * | 11/2003 | Charles et al. ................ | 257/783 |
| 2010/0005865 A1 * | 1/2010 | Miura .......................... | 73/54.41 |

OTHER PUBLICATIONS

Aydin, EM et al. "Plane-Couette flow between smooth and rough walls", Experiments in Fluids, vol. 11, 1991, pp. 302-312.

* cited by examiner

*Primary Examiner* — Lisa Caputo
*Assistant Examiner* — Jamel Williams
(74) *Attorney, Agent, or Firm* — Merchant & Gould P.C.

(57) ABSTRACT

A device for determining material properties includes a bottom panel extending from a first end to a second end of the device, for supporting a material to be tested. A closed loop flexible wall extends upwardly from the panel and is in operational engagement with a flexible wall idle means towards the first end of the device and a flexible wall driving means in spaced relation with the flexible wall idle means. The flexible wall driving means causes movement of the closed loop flexible wall along a predetermined closed loop path. The flexible wall driving means and the means of driving it are arranged at a position outside of a material containment area of the device.

25 Claims, 8 Drawing Sheets

DEVICE FOR DETERMINING MATERIAL PROPERTIES

This application claims benefit of Serial No. 2012901433, filed 12 Apr. 2012 in Australia and which application is incorporated herein by reference. To the extent appropriate, a claim of priority is made to each of the above disclosed applications.

TECHNICAL FIELD

The present invention relates to a device for determining material properties. The device can be used to measure the mechanical properties, such as shear strength and viscosity, of any flowable material, including complex materials such as soils, granular materials, powders, suspensions, emulsions, colloids and melted polymers.

The device has applications in many industries such as mining, geotechnical engineering and civil engineering projects in which it is desired to know the properties and failure behaviour of e.g. soil or sand under certain loading conditions. The information gathered using the device is important to the design of building foundations, pipework, tunnel construction, and also for use in landslide and earthquake management structures.

The device also has application in the food industry, agriculture, bio engineering, chemical engineering, mechanical engineering, material processing, petroleum engineering, pharmaceutics, as well as the cosmetics and paint industries. The information gathered using the device is then useful to improving efficiency and optimising processes.

BACKGROUND OF THE INVENTION

The testing of flowable solid materials such as soil, sand and liquids for their mechanical properties such as shear strength and viscosity has long been an important aspect in the design of, for example, building foundations, earthworks, underground pipe installations, new liquid products such as paints, cosmetics and foodstuffs. This is usually done by deforming samples of the materials and measuring the corresponding bulk relationships connecting nominal stress, strain, and their rates of change. Bulk properties such as the material strength and viscosity are then obtained from these relationships. Several devices with various geometries already exist and are in routine use. For example, the tri-axial apparatus, the Couette rheometer and the plane-Couette rheometer are described below.

FIG. 1 shows a known device for determining material properties, being a tri-axial apparatus 1 in which the material 2 to be tested is supported on a base 3 and is sealed within a rubber membrane 7 that is surrounded by water 4 in a confining cylinder 5. A load 6 is applied to the material from above. A disadvantage of this device is that the material 2, for example soil, bulges within the rubber membrane 3 as it is compressed. Furthermore, the soil tends to fail along a localised failure zone, or plane, within the bulk material causing the rubber membrane 3 to further shift and deform. As a result, the movement of the rubber membrane 3 interacts with the soil deformation. As a result, the material behaviour along the localised failure cannot be isolated and measured and bulk measurements of the material sample cannot provide reliable data about the properties determining the emergence of the localised failure. A disadvantage of this device is thus that it is limited to only measuring material properties undergoing low levels of deformation that do not cause material failure.

FIG. 2 shows another known device for material properties, being a cylindrical Couette shear device 10. The Couette shear device 10 comprises an inner cylinder 11, a concentric outer cylinder 12 and an annular testing space 13 formed between the two cylinders. The material to be tested is placed in the annular space 13 and the outer cylinder 12 is rotated relative to the inner cylinder 11. The rotation creates a continuous shear strain within the material. However, due to the cylindrical geometry, the stresses produced within the material diminish radially from the inner cylinder 11 towards the outer cylinder 12. As such, the stresses and the strain rate are intrinsically heterogeneous. The device thus has the same disadvantage as the tri-axial apparatus, in that the bulk measurement of strain cannot accurately reflect the true strain gradients within the bulk material due to the non-homogeneity of the material deformation.

A further known device is a plane Couette device (not shown), which comprises a pair of rotating cylinders and a flexible belt arranged around the cylinders. The belt and cylinders are placed inside a tank and the entire apparatus is filled with water. The belt is driven by one of the cylinders to create a shear flow inside the belt. This device produces a continuous shear flow inside the belt, but it has the disadvantage that the fluid sample is allowed to flow both inside and outside the belt. Any measurement of the shear strength and viscosity of the fluid is therefore not representative for a fixed material sample. This 'open' system also makes it almost impossible to control the confining stresses applied to the fluid. This is a major issue for most of the complex materials mentioned above, since the confining stresses play a crucial role in determining their mechanical behaviour and thus interpreting their properties.

OBJECT OF THE INVENTION

It is the object of the present invention to substantially overcome or at least ameliorate one or more of the above disadvantages.

SUMMARY OF THE INVENTION

There is disclosed herein a device for determining material properties, the device including:
a first end;
a second end;
a bottom panel, extending from the first end to the second end, for supporting a material to be tested;
a closed loop flexible wall arranged to extend upwardly from the bottom panel;
a flexible wall idle means disposed towards the first end of the device;
a flexible wall driving means disposed in spaced relation with the flexible wall idle means;
the closed loop flexible wall being arranged in operational engagement with the flexible wall idle means and the flexible wall driving means so that movement of the flexible wall driving means causes movement of the closed loop flexible wall along a pre-determined closed loop path;
means to drive the flexible wall driving means; and
means for measuring one or more properties of the material to be tested;
wherein the bottom panel and the closed loop flexible wall together form a material containment area therewithin, and wherein the flexible wall idle means, the flexible wall driving means and the means for driving the flexible wall driving means are each arranged at a position outside of the material containment area.

An advantage of the device is that a continuous shear strain can be applied to a material to be tested simply by applying a torque to the flexible wall driving means such that it causes movement of the flexible wall in a pre-determined path. The device is capable of shearing a material sample continuously and as homogeneously as possible, whilst also providing the means to impose normal 'confining' stresses on the material sample if desired.

The flexible wall and bottom panel forms a material containment area whose bulk geometry is substantially fixed—it does not substantially deform as the material to be tested deforms under load. As such, the bulk material deformation is not adversely affected by changes to the device geometry, in contrast to the known triaxial apparatus.

Furthermore, the arrangement of the flexible wall idle means, the flexible wall driving means and the means for driving the flexible wall driving means outside of the material containment area allows the material to flow inside the flexible wall, unhindered by the proximity of the flexible wall driving means and flexible wall idle means, for as long as a torque is applied to the flexible wall driving means. The result is a near homogeneous deformation of the material; the strain gradients across the material at any point within the material containment area are substantially homogeneous throughout. This has the advantage that there are no localised failures and the bulk measurement of a property such as shear strain within the material will be representative for the bulk material sample. Tests can therefore be conducted at higher loads than is the case with either the triaxial apparatus or the cylindrical Couette shear device.

In a preferred embodiment, the flexible wall driving means is any one of a driving wheel, pulley, gear or cog arranged in operational engagement with the closed loop flexible wall.

Preferably, the flexible wall is arranged to wrap around the flexible wall driving means towards the second end of the device. Preferably, the position of at least one of the flexible wall driving means and the flexible wall idle means is adjustable along an axis defined between the first end and the second end of the device. Alternatively, the flexible wall driving means is disposed outside of the closed loop flexible wall.

In a preferred embodiment, the flexible wall idle means is any one of a passive wheel, pulley, gear, or cog.

Preferably, the closed loop flexible wall is arranged to wrap around the flexible wall idle means towards the first end of the device. In the alternative embodiment in which the flexible wall driving means is disposed outside of the flexible wall, a second flexible wall idle means is preferably disposed towards the second end of the device and the closed loop flexible wall is arranged to wrap around both the first and the second flexible wall idle means. In either embodiment, the flexible wall preferably moves along a rectangular-oval, obround or 'stadium' shaped path.

Preferably, the closed loop flexible wall is notched for engagement with the flexible wall driving means and the flexible wall idle means.

Preferably, the flexible wall driving means and the flexible wall idle means each comprise one or more teeth at the circumference thereof for engagement with the closed loop flexible wall.

In a preferred embodiment, the flexible wall comprises a belt. Alternatively, the flexible wall comprises a chain or a set of articulated panels.

Preferably, the closed loop flexible wall is arranged to include two generally parallel straight sections extending between the first end and the second end of the device and semi-circular recirculation zones at each of the first end and the second end thereof. In a preferred embodiment, a means of applying a lateral inward force to the closed loop flexible wall is provided at at least one location along at least one of the straight sections.

Preferably, a friction reducing means is provided between the closed loop flexible wall and the means of applying a lateral inward force to the closed loop flexible wall.

More preferably, the friction reducing means includes any one of at least one roller, at least one ball bearing or a lubricant.

Preferably, the means for driving the flexible wall driving means includes a motor for applying torque to the belt driving means. More preferably, the motor is a variable speed motor.

Preferably, the material containment area includes a pre-determined maximum fill level for the material to be tested.

Preferably, the device includes a means of applying a controlled load to the material from above the device.

Preferably, the device includes a top panel adapted to be positioned over the material to be tested within the material containment area.

Preferably, the means for measuring one or more properties of the material to be tested includes at least one of a torque meter, a strain gauge, a load cell, a proximity sensor, a particle image velocimetry apparatus, a thermal camera or an accelerometer.

Preferably, at least one of the top panel and the bottom panel is made of a transparent material.

Preferably, the device is housed in an outer sealed enclosure.

BRIEF DESCRIPTION OF THE DRAWINGS

A preferred embodiment of the present invention will now be described, by way of an example only, with reference to the accompanying drawings wherein.

DETAILED DESCRIPTION OF THE PREFERRED EMBODIMENTS

Figure 1:
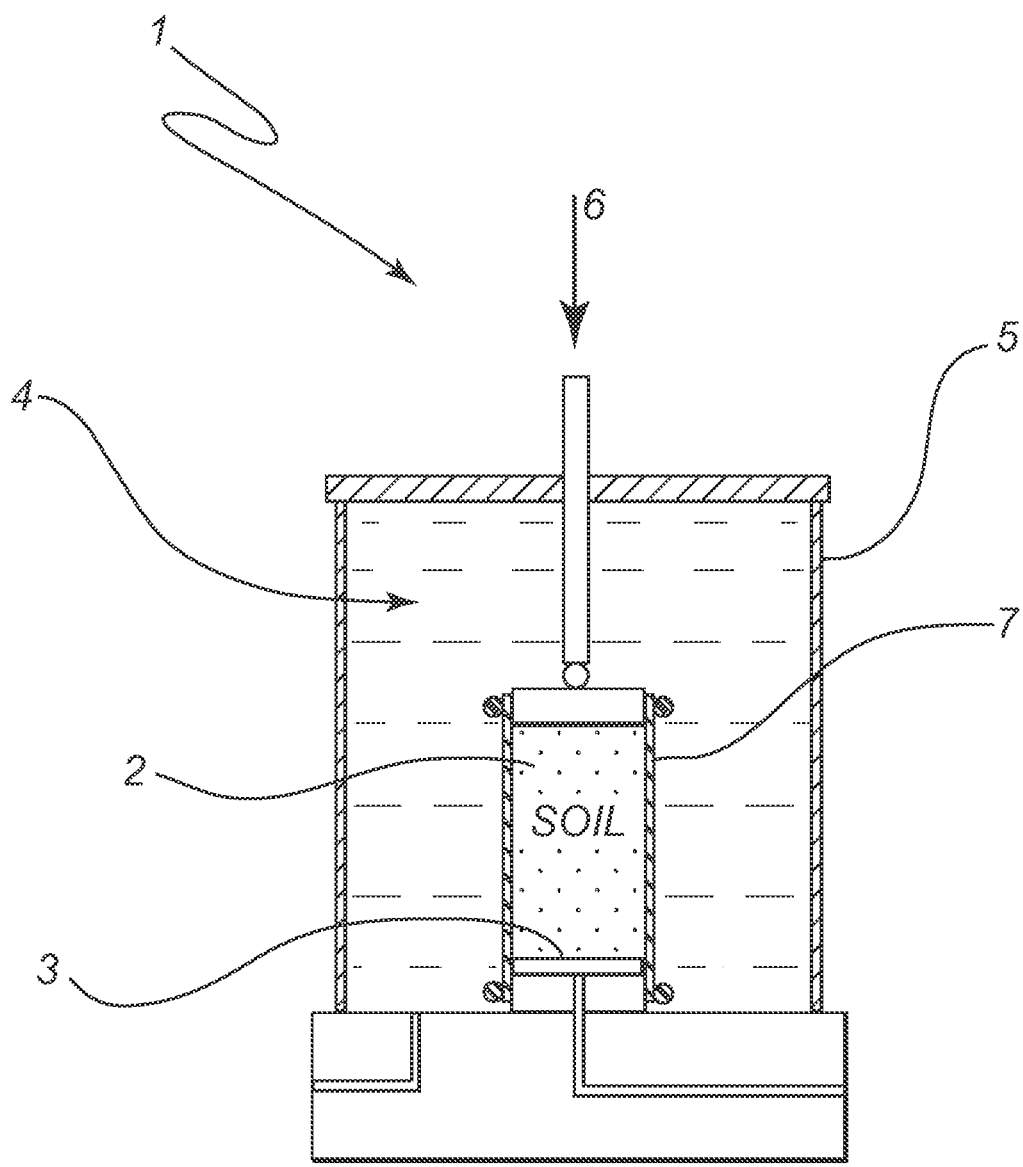
FIG. 1 is a schematic representation of a prior art device.
Figure 2:
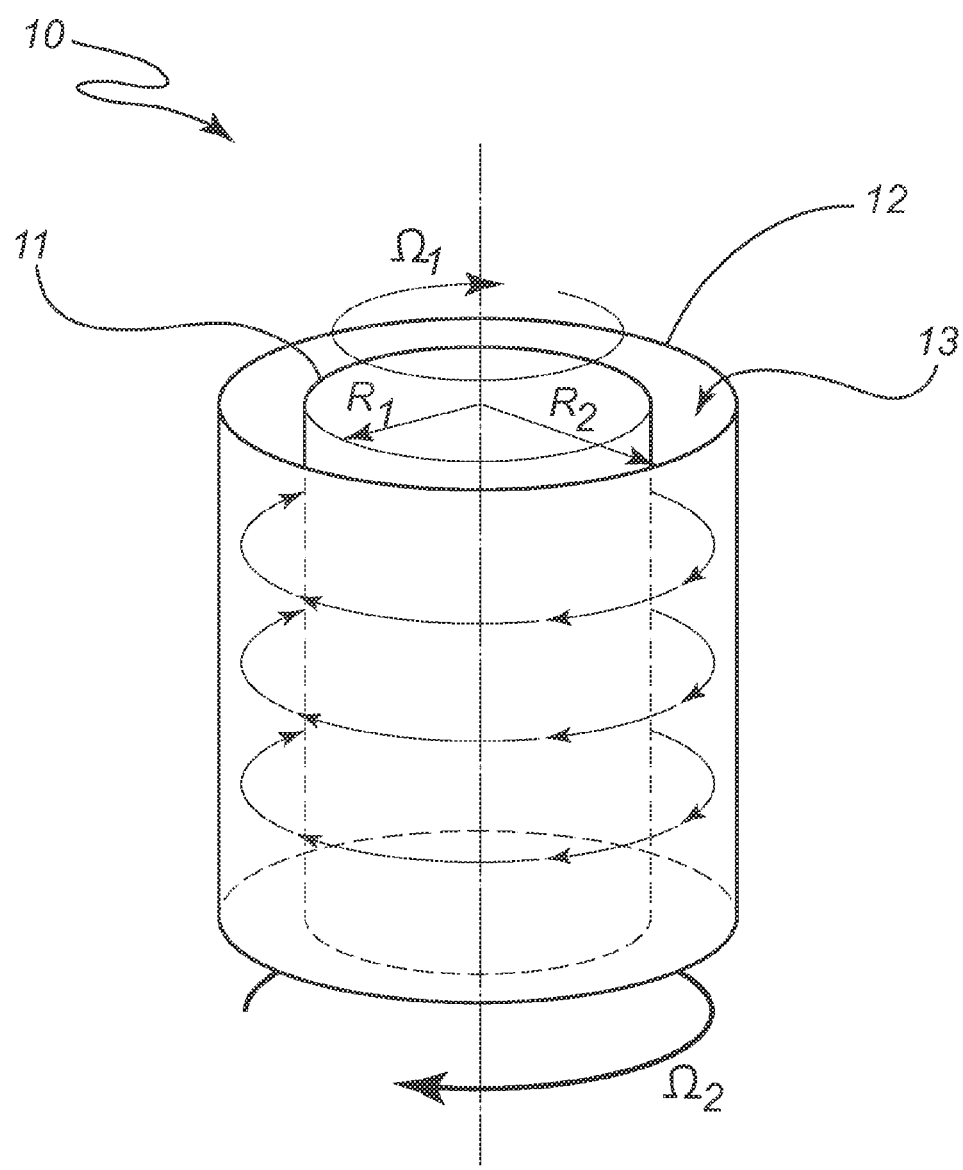
FIG. 2 is a schematic representation of another prior art device.
Figure 3:
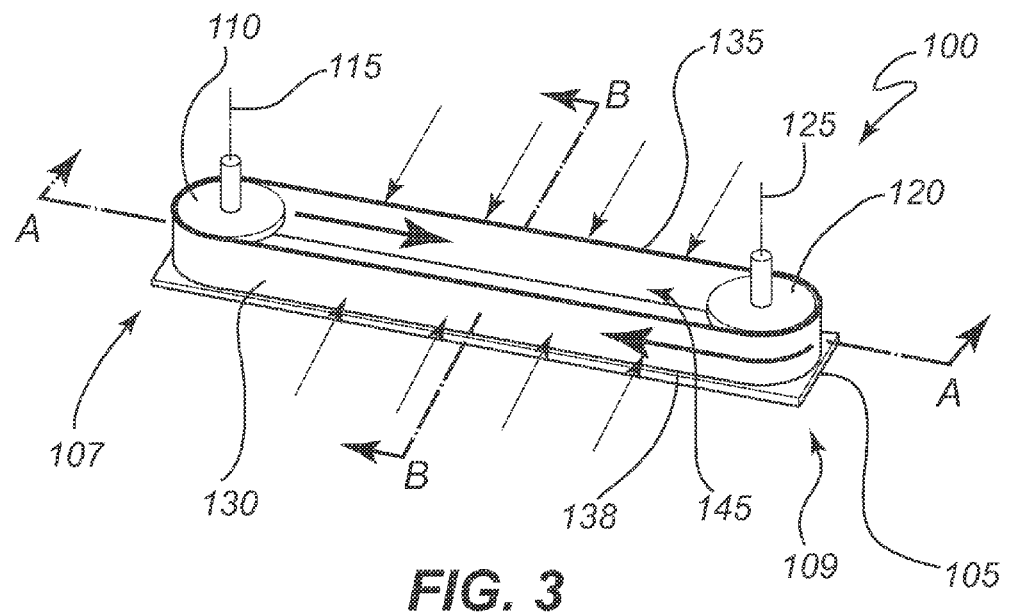
FIG. 3 is a schematic representation of a device in accordance with the present invention.

FIGS. 3, 4, 5 and 10, show a first embodiment of a device 100 for determining material properties. The device 100 has a first end 107 and a second end 109. The device 100 includes a rigid, elongate fixed bottom panel 105, seen in FIGS. 3, 4 and 5. The fixed bottom panel 105 is made of a material that is rigid enough that it does not bend under load. In the embodiment shown, the fixed bottom panel is made of transparent material such as glass. This allows material measurements to be taken through the transparent panel using particle image velocimetry or a thermal imaging camera or the like.

A closed loop flexible wall 130 extends upwardly from the bottom panel 105. The flexible wall 130 is moveable along a pre-determined path and is driven by a flexible wall driving means 110.

The flexible wall driving means is in the form of a driving wheel 110 that is suspended on a gantry 112 (seen only in FIG. 10) above the first end 107 of the device 100. The driving wheel 110 has a central axis 115 that is perpendicular to the plane of the fixed bottom panel 105 such that the plane of the wheel 110 itself is parallel to the fixed panel 105. The driving wheel 110 is operationally connected to a motor 117 (shown in FIG. 10) via one or more gearboxes (not shown). The motor 117 is an electric or thermic motor that is operable at a desired variable speed, or under a desired torque.

A flexible wall idle means, in the form of an idle wheel 120 having the same diameter as the driving wheel 110, is suspended on a gantry 122 (not shown) above the second end 109 of the device 100 at the same height as the driving wheel 110. The idle wheel 120 has a central axis 125 that is perpendicular to the plane of the fixed bottom panel 105 such that the plane of the wheel 120 itself is parallel to the fixed panel 105.

The closed loop flexible wall 130 has an upper edge 135 and a lower edge 138. In this embodiment, the flexible wall 130 is a belt. The upper edge 135 of the belt 130 wraps around each of the driving wheel 110 and the idle wheel 120 such that the closed loop wall 130 has two parallel straight sides and a semi-circular recirculation portion at each of the first end and the second end where the belt engages with the driving wheel 110 and the idle wheel 120. In use, the belt therefore moves along a rectangular-oval, obround or 'stadium' shaped path.

The area within the belt 130, above the fixed bottom panel 105 and below the driving wheel 110 and idle wheel 120 forms a material containment area 145. The material containment area 145 has a maximum fill level, below the driving wheel 110 and the idle wheel 120, for a material to be tested marked thereon. The maximum fill level is set such that the material within the containment area 145 will be allowed to dilate, without touching the driving wheel 110 and idle wheel 120. The positioning of the flexible wall idle means, flexible wall driving means and the motor outside the material containment area means that the drive system does not disturb the material to be tested and the material can freely recirculate within the moving flexible wall Referring now to FIGS. 6 to 9, the device 100 also includes a removable top panel 150. The top panel 150 is insertable into the material containment area 145 beneath the driving wheel 110 and the idle wheel 120 such that it completely covers the material 101. The top panel 150 provides a cover for the material and can also be used to impart a normal confining vertical stress to the material. In the embodiment shown, the top panel 150 is made of a transparent material such as glass to facilitate material measurement using particle image velocimetry or a thermal imaging camera or the like.

The flexible wall or belt 130 is made of a flexible material that is chosen to adequately support the material laterally within the containment area 145 without its geometry altering substantially under load. The belt 130 must however be flexible enough to allow for minor deformation in order to function to transfer a normal lateral force applied to it to the material 101 itself. In the example of the device shown in FIG. 10, the belt 130 is a metallic automotive belt. The belt 130 is notched for engagement with the driving wheel 110 and idle wheel 120. The driving wheel 110 and idle wheel 120 are each provided with a plurality of teeth 118 (see in FIGS. 6 and 10) around the circumference thereof for engagement with the belt 130.

In an embodiment, the material of the flexible wall is chosen to have a surface roughness similar to the surface roughness of the tested material. For example, the material of the flexible wall may be chosen to have a roughness similar to a specific material such as concrete or stone when the tested material is sand, gravel, clay or silt.

In the embodiment shown, a distance between the two straight parallel sections is between about 1 mm to 1 m, although it may be more or less than this.

The distance between the two re-circulation portions is between about 1 cm to 5 m, although it may be more or less than this.

The height of the flexible wall is about 1 cm to 1 m, although it may be shorter than 1 cm or taller than 1 m.

The device 100 dimensions are selected according to the material to be tested. For instance, if a very expensive material is to be tested, a small device is appropriate. A large device is appropriate for testing granular materials having large grains.

The aspect ratio may be selected to reduce the relative contribution of the flexible wall 130 on the measurements to be taken. A tall flexible wall 130 may limit the relative effect of any friction at the surface of the bottom panel 105 and/or the top panel 150 on the material sample. A small distance between the parallel sections should limit the relative effect of the two recirculation portions on the material sample.

In an alternative embodiment, the bottom panel 105 and/or the top panel 150 is made of stainless steel or other material that is not subject to chemical reaction whilst it is in contact with the material to be tested. The device 100 may include more than one idle wheel 120, more than one driving wheel 110 and more than one motor 117, if desired.

Figure 4:
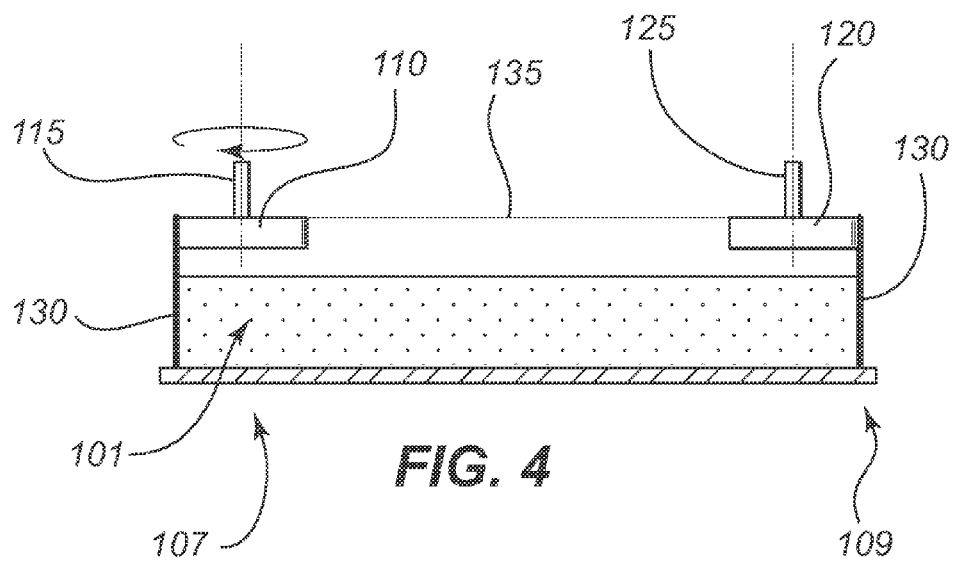
FIG. 4 is a schematic representation of the device of FIG. 3 along a section A-A.
Figure 5:
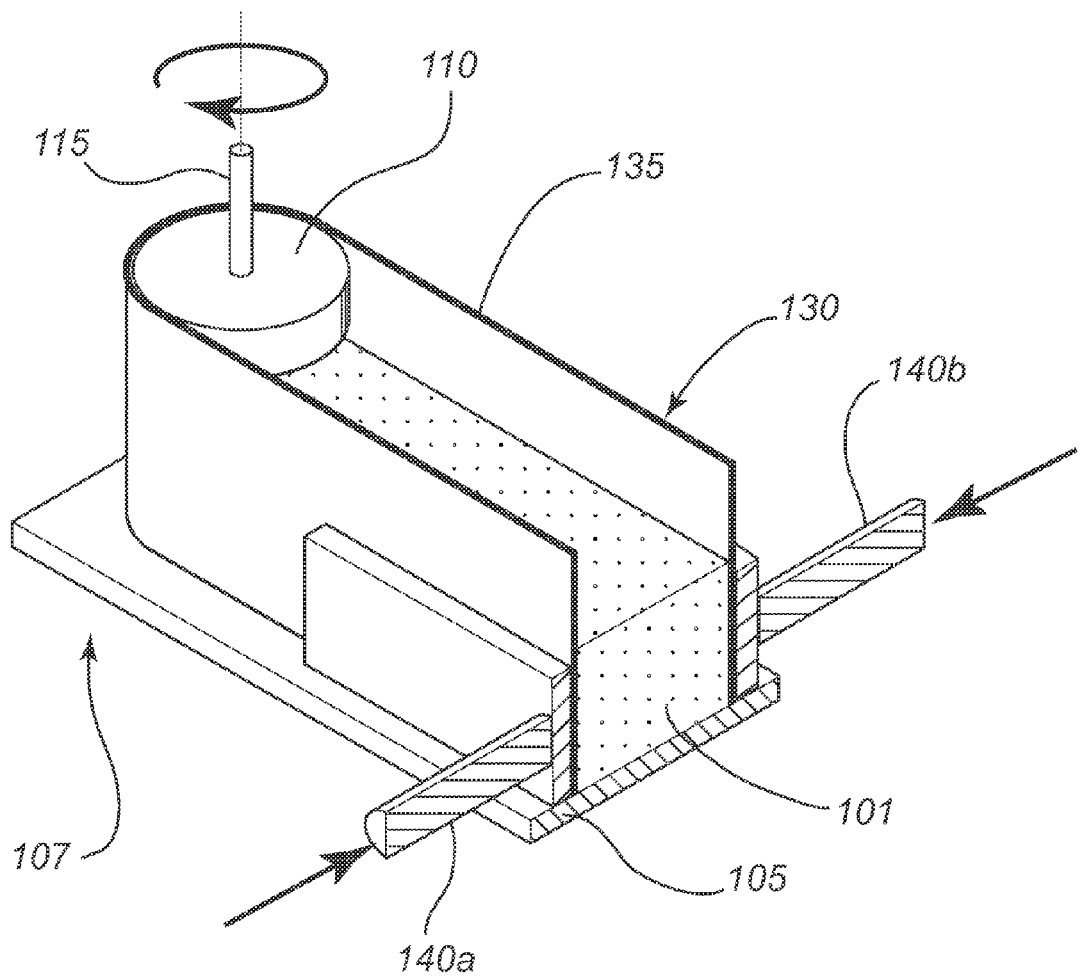
FIG. 5 is a schematic representation of the device of FIG. 3 along a section B-B.
Figure 6:
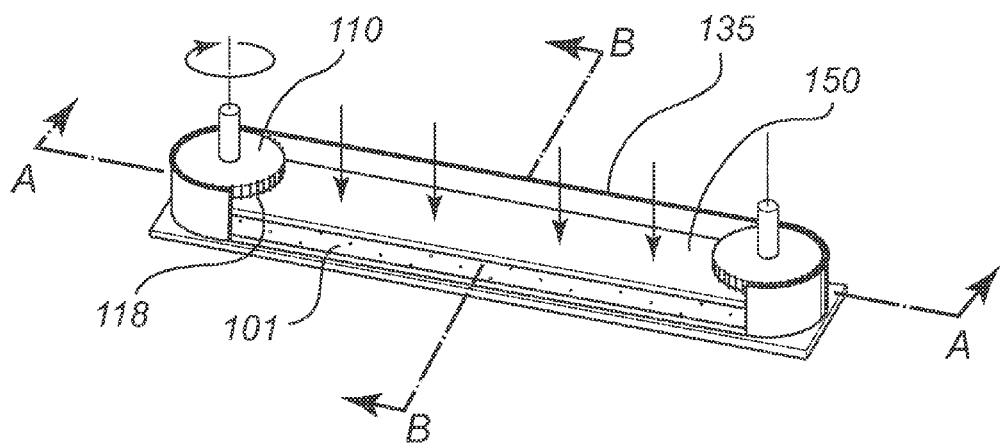
FIG. 6 is a schematic representation of the device of FIG. 3, including a top panel.

FIGS. 4 and 5 show schematically how the device 100 is loaded to create deformation of the material 101 to be tested.

A torque is applied to the driving wheel 110 via motor 117. The motor can be operated at constant or variable speed. The torque needed to maintain the constant or variable speed can then be measured by a torque meter. Alternatively, the motor can be operated at a constant or variable torques and the corresponding speed of the belt can be measured via a tachometer. The applied torque causes the driving wheel 110 to rotate (clockwise in the embodiment shown) which in turn causes the belt 130 to move clockwise along the oval/obround shaped path. The belt 130 moves continuously in the oval/obround shaped loop whilst the motor 117 is switched on and is connected to the driving wheel 110. The parallel motion of the belt walls between the driving wheel 110 and the idle wheel 120 applies a shear strain to the material 101 that is proportional to the speed of the motor 117. Accordingly, the shear strain rate within the material can be measured or controlled by dividing the velocity difference of the parallel belt walls by their distance. The shear force is measured or controlled by equating the torque measured by the torque meter to the moment from the coupled shear forces exerted on the wheels by the parallel belt walls. Alternatively, strain gauges and a load cell may be applied directly to the parallel belt walls in order to take strain measurements.

A normal lateral load is applied to the exterior of the belt 130 via lateral load members 140a, 140b along the elongate sides of the belt between the driving wheel 110 and the idle wheel 120. Application of the normal lateral force to the belt places the material under normal lateral stress and creates a normal lateral strain in the test material. The normal lateral force is applied using known experimental techniques that are standard in the art. The lateral stress acting normal to the belt walls is obtained by dividing the force applied on the walls by their area. The corresponding normal strain rate is obtained or controlled by dividing the normal relative velocity of the lateral belt walls by their distance.

Figure 10:
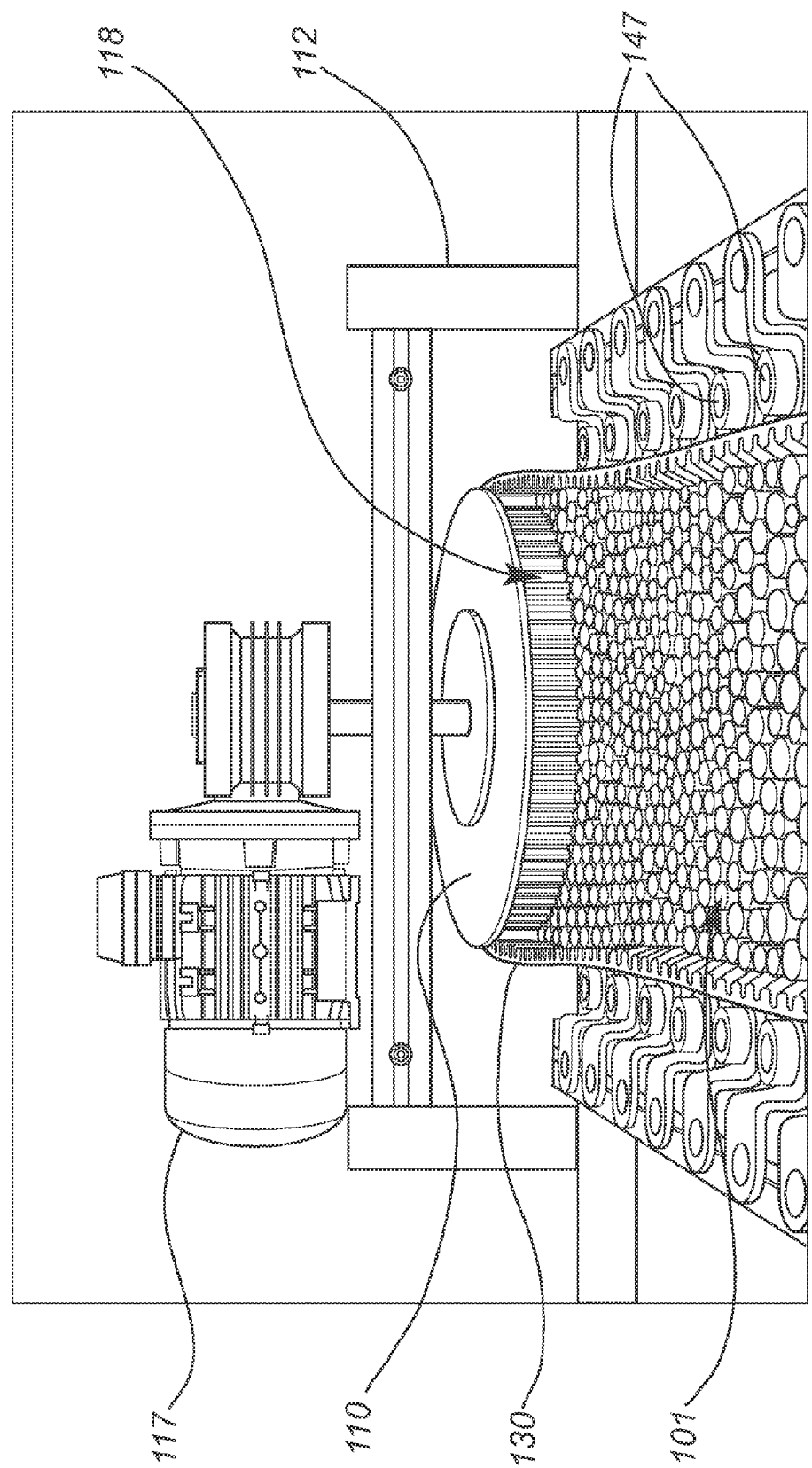
FIG. 10 is a photograph of an embodiment of the device shown without a top panel or confining case.

Application of a normal lateral load to the belt 130 may generate undesirable friction that will affect the true application of the load to the test material. The friction at the interface between the load members 140a, 140b and the belt 130 is reduced using one or more rollers 147 positioned externally of the belt as shown in FIG. 10, between the belt and the loading members 140a, 140b. In alternative embodiments, the rollers 147 may be replaced with ball bearings, lubricants or other friction reducing means as will be apparent to the skilled person in the art. Where rollers or ball bearings are positioned externally of the belt 130, they provide an additional rigidity to the belt 130 in functioning to contain the material 101 within the material containment area 145 when the device 100 is under load.

Figure 7:
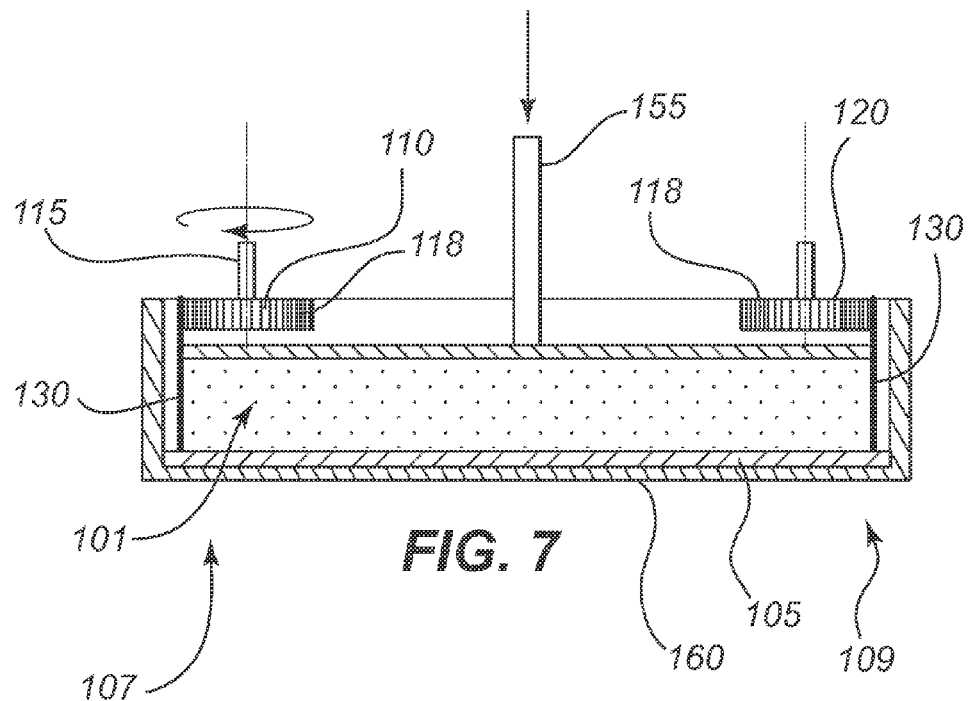
FIG. 7 is a schematic representation of the device of FIG. 6 along a section A-A.
Figure 8:
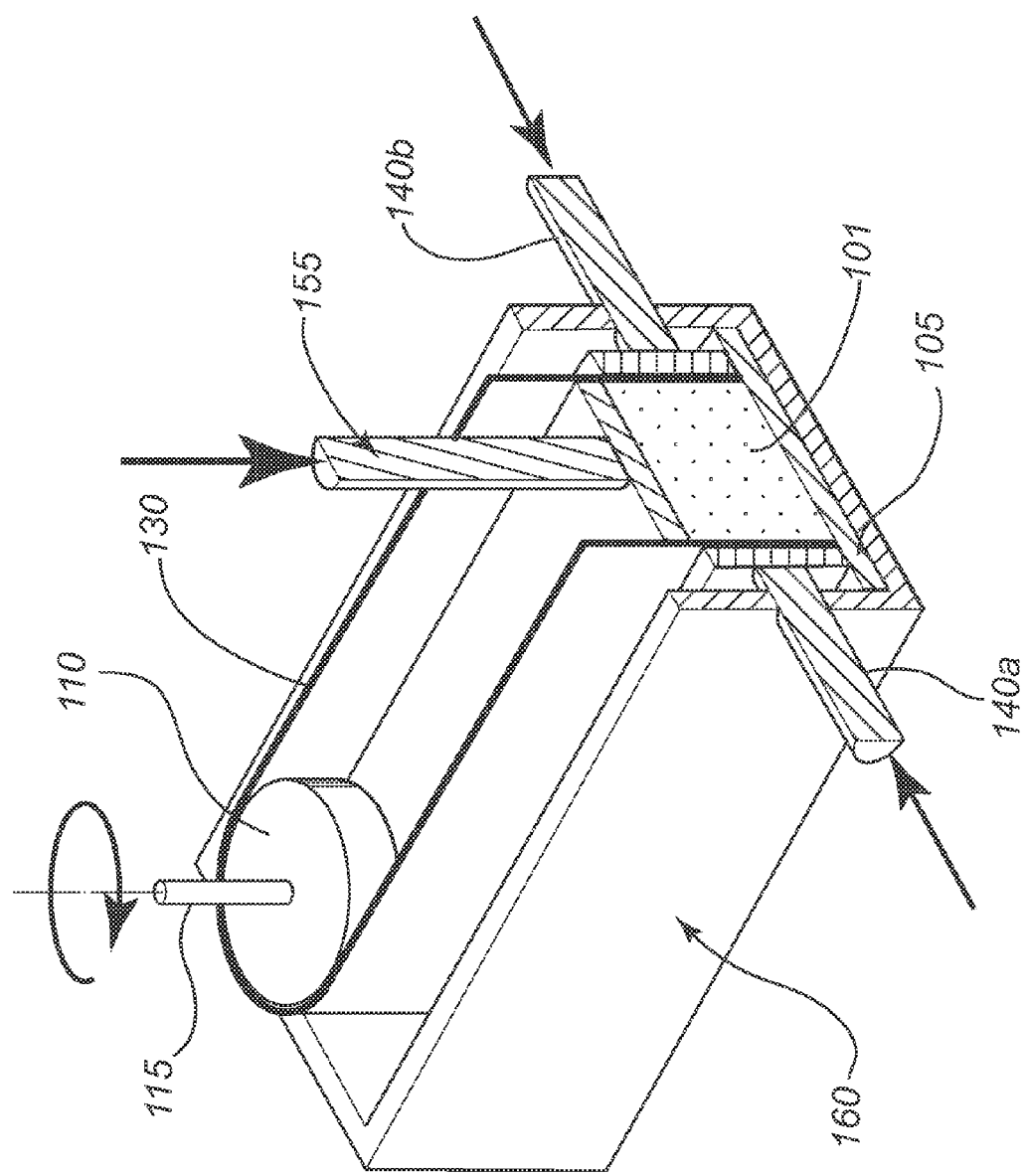
FIG. 8 is a schematic representation of the device of FIG. 6 along a section B-B, shown enclosed in a confining case (lid removed)
Figure 9:
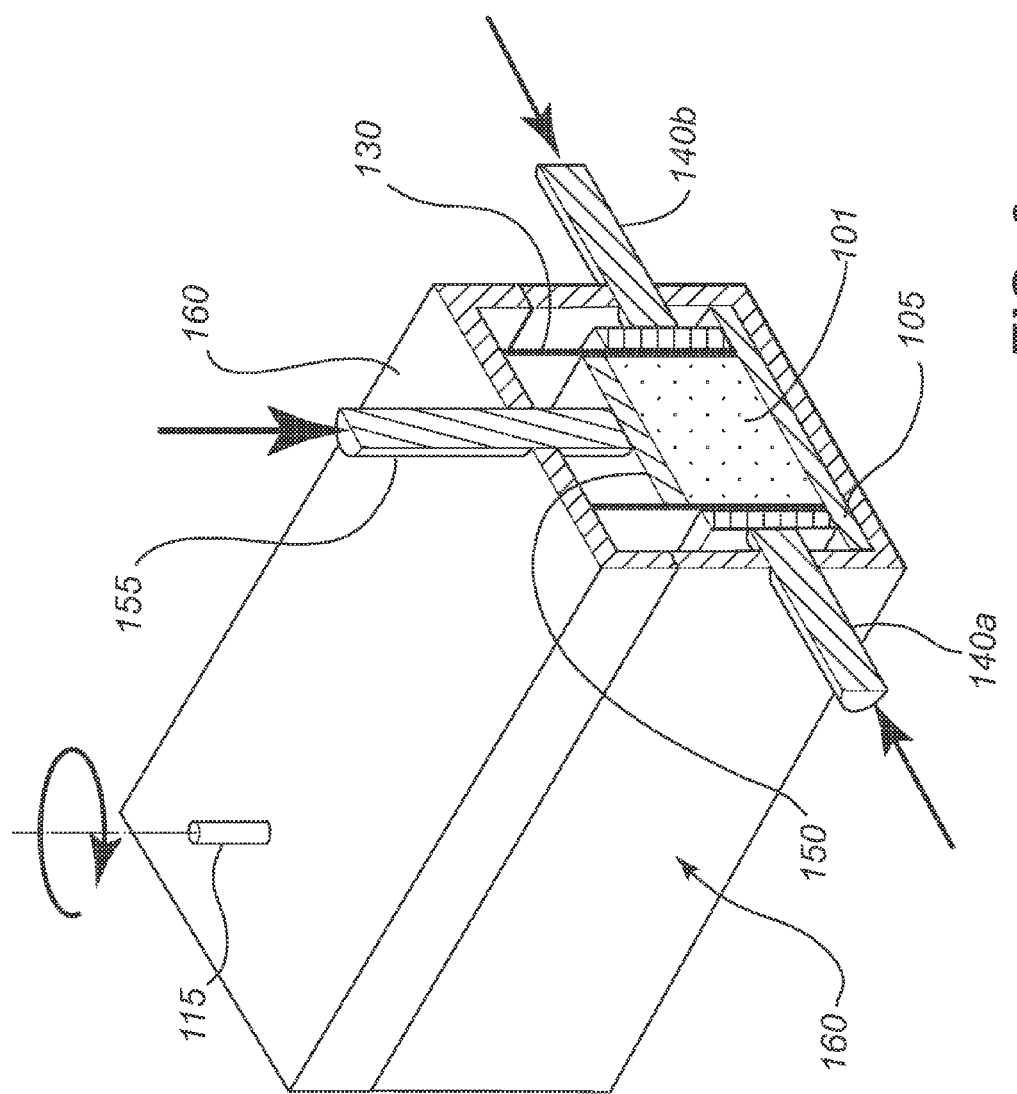
FIG. 9 is a schematic representation of the device of FIG. 8 shown with the lid in place.

The top panel 150 itself provides a compressive load above the material 101. An additional vertical normal force is applied from above the device via a vertical load member 155 attached to the top panel 150 (FIGS. 7 to 9). The application of a normal vertical force places the material under normal vertical stress. As with the lateral load members 140a and 140b, the normal vertical force is applied using known experimental techniques that are standard in the art. Normal vertical stress can be measured or controlled by dividing the normal vertical force by the area of the top panel. Normal vertical strain rate can be measured or controlled by dividing the velocity of the top panel by the sample height.

FIGS. 8 and 9 show the device 100 housed in an optional confining case 160 that surrounds the entire device 100 such that it is sealed other than for the application of normal lateral, normal vertical and torque loads. In an embodiment, water is added into the casing 160 to generate an isotropic stress on the belt 130 and top panel 150. Such an experiment can be useful for the testing of materials that are intended for underwater use.

Furthermore, the confining case 160 provides an extra rigidity to the device 100 and it functions to contain the material 101 being tested in the event that the belt 130 should buckle under load.

The device 100 may be operated as follows. Firstly, it must be determined as to which mechanical property of the material is to be measured. A corresponding force or deformation is then applied to the material in order to place the material under stress. For example, if it is desired to measure shear strain rate, a torque is applied to the driving wheel to apply a designated shear stress to the material via the belt 130. Continuous movement of the belt is measured and takes an oval, obround or stadium-like path that causes corresponding continuous flow of the material such that a measurable, near-homogeneous, bulk strain rate develops throughout the bulk material.

The bulk material boundary formed by the belt 130 does not substantially change under load, therefore measurement of the bulk shear strain will not be affected by changes in the belt geometry. The overall result is a significant improvement in the reliability of the bulk shear strain measurement within the material.

Similarly, if it is desired to measure lateral strain rate then a designated normal lateral force is applied to the belt 130 using load members 140a, 140b.

If a normal vertical strain rate is to be measured then a designated compressive vertical force is applied to the material via the top panel 150 and the vertical load member 155, in such a way that the normal vertical stress is controlled and strain rate is measured. Alternatively, if a normal vertical stress is to be measured then a compressive vertical deformation is applied to the material via controlled motion of the top panel 150 using the vertical load member 155, and then measuring the corresponding compressive vertical force.

Each of the forces applied to the material is controllable via adjustment of either the speed of the motor 117 to adjust the torque or adjustment of the normal load applied laterally or vertically to the material.

A combination of forces can also be applied simultaneously to the material to simulate a desired real life loading situation. As such, the device is very versatile and has widespread applications in many industrial sectors.

Although the invention has been described with reference to preferred embodiments, it will be appreciated by those skilled in the art that the invention may be embodied in many other forms without departing from the scope of the invention.

The invention claimed is:

1. A device for determining material properties, the device including:
 a first end;
 a second end;
 a bottom panel, extending from the first end to the second end, for supporting a material to be tested;
 a closed loop flexible wall arranged to extend upwardly from the bottom panel;
 a flexible wall idle means disposed towards the first end of the device;
 a flexible wall driving means disposed in spaced relation with the flexible wall idle means;
 the closed loop flexible wall being arranged in operational engagement with the flexible wall idle means and the flexible wall driving means so that movement of the flexible wall driving means causes movement of the closed loop flexible wall along a pre-determined closed loop path;
 means to drive the flexible wall driving means; and
 means for measuring one or more properties of the material to be tested;
 wherein the bottom panel and the closed loop flexible wall together form a material containment area therewithin, and wherein the flexible wall idle means, the flexible wall driving means and the means for driving the flexible wall driving means are each arranged at a position outside of the material containment area.

2. The device of claim 1, wherein the flexible wall driving means is any one of a driving wheel, pulley, gear or cog arranged in operational engagement with the closed loop flexible wall.

3. The device of claim 1, wherein the flexible wall is arranged to wrap around the flexible wall driving means towards the second end of the device.

4. The device of claim 1, wherein the position of at least one of the flexible wall driving means and the flexible wall idle means is adjustable along an axis defined between the first end and the second end of the device.

5. The device of claim 1, wherein the flexible wall driving means is disposed outside of the closed loop flexible wall.

6. The device of claim 1, wherein the flexible wall idle means is any one of a passive wheel, pulley, gear, or cog.

7. The device of claim 1, wherein the closed loop flexible wall is arranged to wrap around the flexible wall idle means towards the first end of the device.

8. The device as claimed in claim 5, wherein a second flexible wall idle means is disposed towards the second end of the device and the closed loop flexible wall is arranged to wrap around both the first and the second flexible wall idle means.

9. The device of claim 7, wherein the flexible wall is adapted to move along a rectangular-oval, obround or 'stadium' shaped path.

10. The device of claim 1, wherein the closed loop flexible wall is notched for engagement with the flexible wall driving means and the flexible wall idle means.

11. The device of claim 1, wherein the flexible wall driving means and the flexible wall idle means each comprise one or more teeth at the circumference thereof for engagement with the closed loop flexible wall.

12. The device of claim 1, wherein the flexible wall comprises a belt.

13. The device of claim 1, wherein the flexible wall comprises a chain or a set of articulated panels.

14. The device of claim 1, wherein the closed loop flexible wall is arranged to include two generally parallel straight sections extending between the first end and the second end of the device and semi-circular recirculation zones at each of the first end and the second end thereof.

15. The device of claim 14, wherein means of applying a lateral inward force to the closed loop flexible wall is provided at at least one location along at least one of the straight sections.

16. The device of claim 15, wherein friction reducing means is provided between the closed loop flexible wall and the means of applying a lateral inward force to the closed loop flexible wall.

17. The device of claim 16, wherein the friction reducing means includes any one of at least one roller, at least one ball bearing or a lubricant.

18. The device of claim 1, wherein the means for driving the flexible wall driving means includes a motor for applying torque to the belt driving means.

19. The device of claim 18, wherein the motor is a variable speed motor.

20. The device of claim 1, wherein the material containment area includes a pre-determined maximum fill level for the material to be tested.

21. The device of claim 1, wherein the device includes means of applying a controlled load to the material from above the device.

22. The device of claim 1, wherein the device includes a top panel adapted to be positioned over the material to be tested within the material containment area.

23. The device of claim 22, wherein at least one of the top panel and the bottom panel is made of a transparent material.

24. The device of claim 1, wherein the means for measuring one or more properties of the material to be tested includes at least one of a torque meter, a strain gauge, a load cell, a proximity sensor, a particle image velocimetry apparatus, a thermal camera or an accelerometer.

25. The device of claim 1, wherein the device is housed in an outer sealed enclosure.

* * * * *